(12) United States Patent
Osawa et al.

(10) Patent No.: US 10,722,214 B2
(45) Date of Patent: Jul. 28, 2020

(54) ULTRASONIC DEVICE, ULTRASONIC PROBE, AND ULTRASONIC APPARATUS

(71) Applicant: Seiko Epson Corporation, Tokyo (JP)

(72) Inventors: Eiji Osawa, Suwa (JP); Chikara Kojima, Matsumoto (JP)

(73) Assignee: Seiko Epson Corporation (JP)

( * ) Notice: Subject to any disclaimer, the term of this patent is extended or adjusted under 35 U.S.C. 154(b) by 217 days.

(21) Appl. No.: 15/850,799

(22) Filed: Dec. 21, 2017

(65) Prior Publication Data
US 2018/0192995 A1    Jul. 12, 2018

(30) Foreign Application Priority Data
Jan. 6, 2017    (JP) .................. 2017-000917

(51) Int. Cl.
| | | |
|---|---|---|
| B06B 1/06 | (2006.01) | |
| A61B 8/00 | (2006.01) | |
| A61B 8/15 | (2006.01) | |
| A61B 8/08 | (2006.01) | |
| A61B 5/00 | (2006.01) | |
| A61B 8/13 | (2006.01) | |

(52) U.S. Cl.
CPC .............. *A61B 8/4494* (2013.01); *A61B 8/15* (2013.01); *B06B 1/0622* (2013.01); *A61B 5/0035* (2013.01); *A61B 8/08* (2013.01); *A61B 8/0833* (2013.01); *A61B 8/13* (2013.01); *A61B 8/4444* (2013.01); *A61B 8/56* (2013.01); *G01N 2291/106* (2013.01)

(58) Field of Classification Search
CPC ....... A61B 8/4494; A61B 5/0035; A61B 8/15; A61B 8/444
See application file for complete search history.

(56) References Cited

U.S. PATENT DOCUMENTS

| | | | | |
|---|---|---|---|---|
| 5,495,137 | A | * | 2/1996 | Park .................. B06B 1/0688 310/331 |
| 5,600,197 | A | * | 2/1997 | Takeuchi ................ B41J 2/161 310/324 |
| 9,440,258 | B2 | | 9/2016 | Klee et al. |
| 9,772,314 | B2 | * | 9/2017 | Kojima .................. G10K 11/28 |
| 2006/0186762 | A1 | * | 8/2006 | Sugiura ................ B06B 1/0692 310/328 |
| 2009/0295876 | A1 | * | 12/2009 | Kobayashi ............. B41J 2/1646 347/71 |
| 2013/0208572 | A1 | | 8/2013 | Klee et al. |
| 2016/0282454 | A1 | * | 9/2016 | Ohashi ................... G01S 7/521 |
| 2016/0365840 | A1 | | 12/2016 | Klee et al. |

FOREIGN PATENT DOCUMENTS

| | | |
|---|---|---|
| JP | 2010-164331 A | 7/2010 |
| JP | 2011-259274 A | 12/2011 |
| JP | 2013-539254 A | 10/2013 |
| JP | 2016-019012 A | 2/2016 |
| JP | 2016-181842 A | 10/2016 |

* cited by examiner

*Primary Examiner* — J. San Martin
(74) *Attorney, Agent, or Firm* — Harness, Dickey & Pierce, P.L.C.

(57) ABSTRACT

An ultrasonic device includes a substrate that is provided with an opening and a partition wall surrounding the opening, a vibration portion that closes one end side of the opening, and a piezoelectric element that is provided in the vibration portion, in which, in a case where an opening width dimension of the opening is indicated by W, and a thickness dimension of the substrate is indicated by H, a ratio W/H is 0.66 to 0.92.

6 Claims, 8 Drawing Sheets

ULTRASONIC DEVICE, ULTRASONIC PROBE, AND ULTRASONIC APPARATUS

BACKGROUND

1. Technical Field

The present invention relates to an ultrasonic device, an ultrasonic probe, and an ultrasonic apparatus.

2. Related Art

In the related art, there is an ultrasonic device in which a support film closing openings is provided on one surface side of a substrate having the openings, and piezoelectric elements are provided on the support film at positions overlapping the openings (for example, refer to JP-A-2010-164331 and JP-A-2013-539254).

In the ultrasonic device disclosed in JP-A-2010-164331 or JP-A-2013-539254, a partition wall (substrate) is provided to surround the openings, the support film is caused to vibrate by using the piezoelectric elements, and thus ultrasonic waves are output toward the partition wall side of the openings.

Here, in the ultrasonic device disclosed in JP-A-2010-164331, an opening width of the opening is about 100 µm to about several hundreds of µm, and a height of the partition wall (a depth of the opening) is about 100 µm. In the ultrasonic device disclosed in JP-A-2013-539254, an opening width of the opening is 802 µm, and a height of the partition wall is 3 mm (3000 µm).

Meanwhile, in an ultrasonic device having such a configuration, a relationship between an opening width of an opening and a height of a partition wall of the opening (a thickness dimension of a substrate) is an important parameter in performing ultrasonic measurement at high transmission/reception sensitivity.

However, in the above-described ultrasonic device disclosed in JP-A-2010-164331 or JP-A-2013-539254, a relationship between an opening width and a height of a partition wall is not taken into consideration, and sufficient transmission/reception characteristics cannot be obtained.

SUMMARY

An advantage of some aspects of the invention is to provide an ultrasonic device, an ultrasonic probe, and an ultrasonic apparatus having high transmission/reception sensitivity, and, application examples and embodiments thereof will now be described.

An ultrasonic device according to an application example of the invention includes a substrate that is provided with an opening and a partition wall surrounding the opening; a vibration portion that closes one end side of the opening; and a piezoelectric element that is provided in the vibration portion, in which, in a case where an opening width dimension of the opening is indicated by W, and a thickness dimension of the substrate is indicated by H, a ratio W/H is 0.66 to 0.92.

In this application example, the opening is formed by the partition wall surrounding four sides, and the vibration portion is disposed on one end side of the opening. In this ultrasonic device, the vibration portion vibrates when the piezoelectric element is driven, and thus an ultrasonic wave is transmitted. The vibration portion is caused to vibrate due to an ultrasonic wave, and thus a signal is output from the piezoelectric element such that reception of the ultrasonic wave is detected.

Meanwhile, as a result of intensive studies, the present inventor of the present specification has obtained the findings that the transmission/reception sensitivity is changed by the opening width dimension W of the opening and the thickness dimension (a height dimension of the partition wall) H of the substrate, and an ultrasonic device having high transmission/reception sensitivity can be implemented by appropriately setting the opening width dimension W and the thickness dimension H.

In other words, in this application example, the ratio (W/H) between the opening width dimension W of the opening and the thickness dimension H of the substrate is 0.66 to 0.92. In the ultrasonic device, it is possible to increase the reception sensitivity of when an ultrasonic wave (reflected wave) reflected from a subject is received after an ultrasonic wave is transmitted during transmission of the ultrasonic wave. In other words, it is possible to increase the transmission/reception sensitivity in the ultrasonic device.

An ultrasonic device according to an application example of the invention includes a substrate that is provided with an opening and a partition wall surrounding the opening; a support film that closes one end side of the opening, and has a first surface facing the opening and a second surface which is a rear surface of the first surface; a beam portion that joins a sealing plate disposed on the second surface side of the support film to the second surface of the support film; and a piezoelectric element that is provided on the support film, in which the support film includes a vibration portion surrounded by an edge of the partition wall and an edge of the beam portion in a plan view from a thickness direction of the substrate, in which the piezoelectric element is provided in the vibration portion, and, in which, in a case where a width dimension of the vibration portion is indicated by S, and a thickness dimension of the substrate is indicated by H, a ratio S/H is 0.73 to 1.16.

In this application example, the sealing plate is disposed on the substrate on the support film side, and the support film is joined to the sealing plate via the beam portion. In the application example, in the support film closing the opening, for example, a region surrounded by edges of a pair of partition walls facing each other in a plan view and edges of a pair of beam portions facing each other, or a region of which three sides are surrounded by edges of the partition walls and an edge of the beam portion is disposed at one remaining side serves as the vibration portion.

In this application example, the ratio (S/H) between the width dimension S of the vibration portion and the thickness dimension H of the substrate is 0.73 to 1.16. In the ultrasonic device, it is possible to increase the reception sensitivity of when an ultrasonic wave (reflected wave) reflected from a subject is received after an ultrasonic wave is transmitted during transmission of the ultrasonic wave. In other words, it is possible to increase the transmission/reception sensitivity in the ultrasonic device.

An ultrasonic probe according to an application example of the invention includes the ultrasonic device described above; and a casing in which the ultrasonic device is stored.

In this application example, as described above, the transmission/reception sensitivity in the ultrasonic device is high. Therefore, in the ultrasonic probe including such an ultrasonic device, an ultrasonic measurement process can be performed with high accuracy when ultrasonic measurement is performed, and thus it is possible to obtain a highly accurate measurement result.

An ultrasonic apparatus according to an application example of the invention includes the ultrasonic device described above; and a controller that controls the ultrasonic device.

In this application example, as described above, the transmission/reception sensitivity in the ultrasonic device is high. Therefore, in the ultrasonic apparatus, the controller controls the ultrasonic device, and thus it is possible to perform a transmission process or a reception process of an ultrasonic wave with high accuracy.

Consequently, it is possible to perform various ultrasonic processes such as ultrasonic measurement on a subject or ultrasonic therapy on a subject with high accuracy.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

Hereinafter, a first embodiment will be described.

Figure 1:
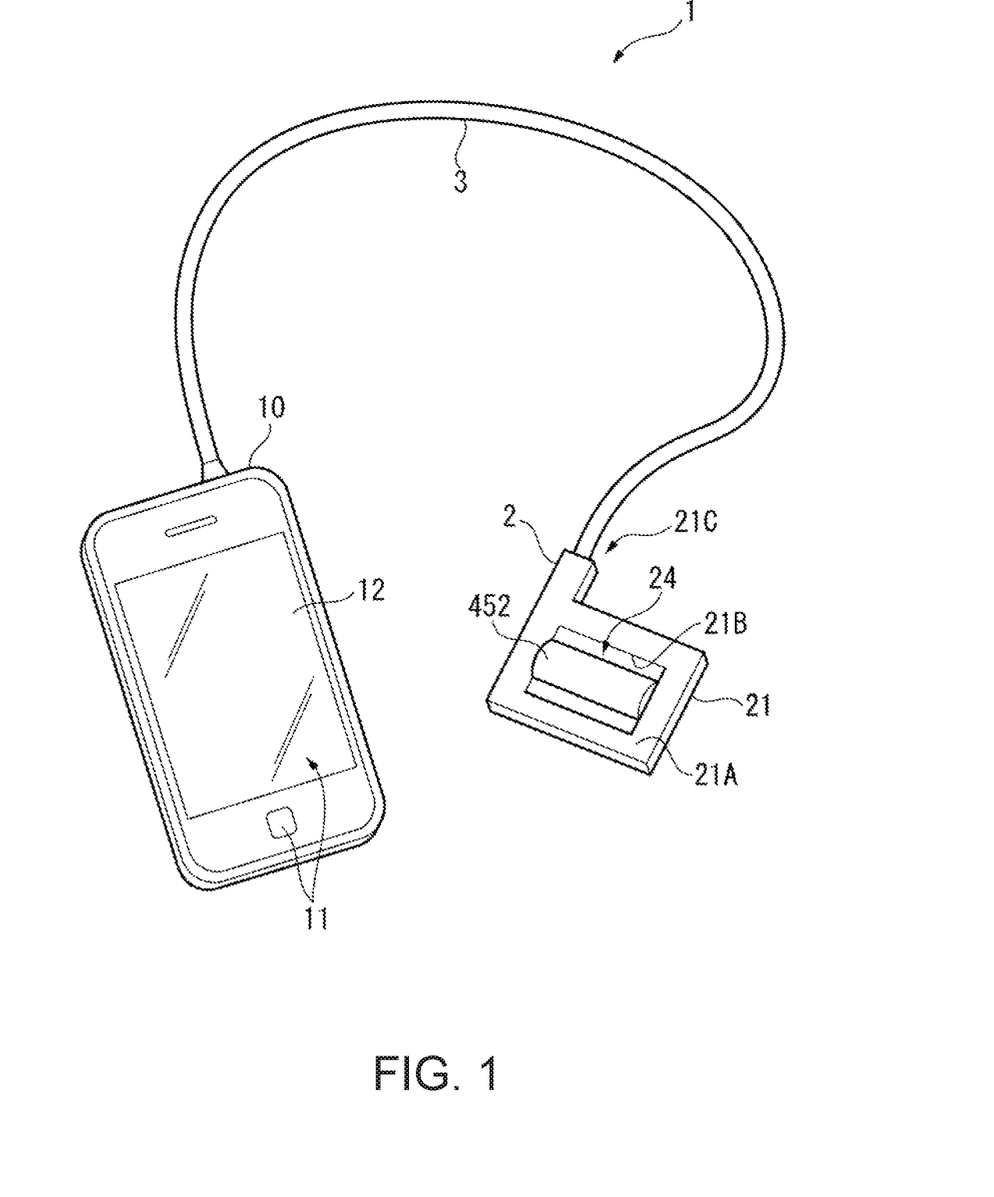
FIG. 1 is a perspective view illustrating a schematic configuration of an ultrasonic measurement apparatus according to a first embodiment.

FIG. 1 is a perspective view illustrating a schematic configuration of an ultrasonic measurement apparatus 1 according to the first embodiment.

The ultrasonic measurement apparatus 1 corresponds to an ultrasonic apparatus, and includes, as illustrated in FIG. 1, an ultrasonic probe 2 and a control device 10 connected to the ultrasonic probe 2 via a cable 3.

The ultrasonic measurement apparatus 1 transmits ultrasonic waves into a subject from the ultrasonic probe 2 in a state in which the ultrasonic probe 2 is brought into contact with a surface of the subject (for example, a living body such as a human body). In the ultrasonic measurement apparatus 1, ultrasonic waves reflected from an organ in the subject are received by the ultrasonic probe 2, and, for example, an internal tomographic image of the subject is obtained or a state (for example, a blood flow) of an organ in the subject is measured, on the basis of a received signal.

Configuration of Control Device

The control device 10 corresponds to a controller, and includes, as illustrated in FIG. 1, an operation unit 11 provided with a button or a touch panel, and a display unit 12. Although not illustrated, the control device 10 includes a storage unit formed of a memory or the like, and a calculation unit formed of a central processing unit (CPU) or the like. The control device 10 causes the calculation unit to execute various programs stored in the storage unit, and thus controls the ultrasonic measurement apparatus 1. For example, the control device 10 outputs a command for controlling driving of the ultrasonic probe 2, forms an image of an internal structure of a subject and displays the image on the display unit 12 on the basis of a received signal which is input from the ultrasonic probe 2, or measures biological information such as a blood flow and displays the biological information on the display unit 12. As the control device 10, for example, a terminal device such as a tablet terminal, a smart phone, or a personal computer may be used, and a dedicated terminal device for operating the ultrasonic probe 2 may be used.

Configuration of Ultrasonic Probe

Figure 2:
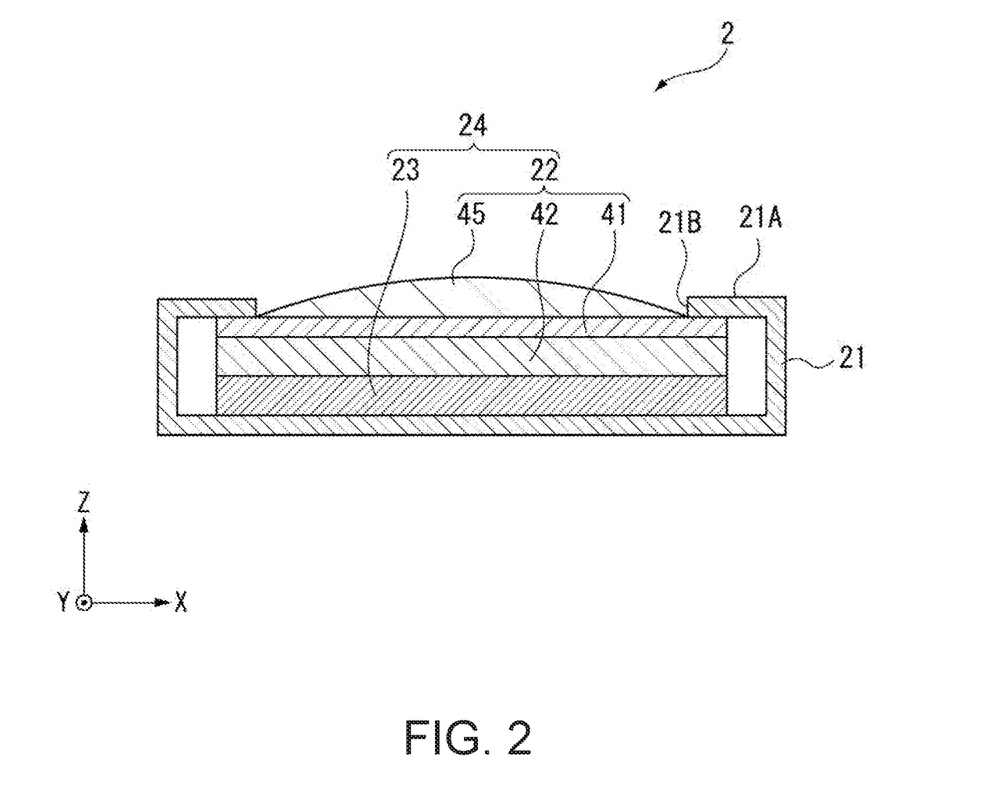
FIG. 2 is a sectional view illustrating a schematic configuration of an ultrasonic probe according to the first embodiment.

FIG. 2 is a sectional view illustrating a schematic configuration of the ultrasonic probe 2.

As illustrated in FIG. 2, the ultrasonic probe 2 includes a casing 21, an ultrasonic device 22 stored in the casing 21, and a circuit substrate 23 provided with a driver circuit and the like for controlling the ultrasonic device 22. An ultrasonic sensor 24 is formed of the ultrasonic device 22 and the circuit substrate 23.

Configuration of Casing

As illustrated in FIG. 1, the casing 21 is formed in a rectangular box shape in a plan view, and is provided with a sensor window 21B on one surface (sensor surface 21A) which is orthogonal to a thickness direction, and a part of the ultrasonic device 22 is exposed to one surface. A passing hole 21C of the cable 3 is provided at a part (a side surface in the example illustrated in FIG. 1) of the casing 21. The cable 3 is inserted into the casing 21 through the passing hole 21C so as to be connected to the circuit substrate 23. A gap between the cable 3 and the passing hole 21C is filled with, for example, a resin material, and thus water resistance is ensured.

In the present embodiment, a configuration example in which the ultrasonic probe 2 is connected to the control device 10 via the cable 3 is described, but this is only an example, and, for example, the ultrasonic probe 2 and the control device 10 may be connected to each other via wireless communication, and various constituent elements of the control device 10 may be provided in the ultrasonic probe 2.

Configuration of Circuit Substrate

The circuit substrate 23 is electrically connected to a drive terminal 431A and a common terminal 433B (refer to FIG. 3) of the ultrasonic device 22 which will be described later, and controls the ultrasonic device 22 under the control of the control device 10.

Specifically, the circuit substrate 23 is provided with a transmission circuit, a reception circuit, and the like. The transmission circuit outputs a drive signal for causing the ultrasonic device 22 to transmit an ultrasonic wave. The reception circuit acquires a received signal output from the ultrasonic device 22 having received an ultrasonic wave, performs an amplification process, an A/D conversion process, a phasing addition process, and the like on the received signal, and outputs the received signal having undergone the processes to the control device 10.

Configuration of Ultrasonic Device

Figure 3:
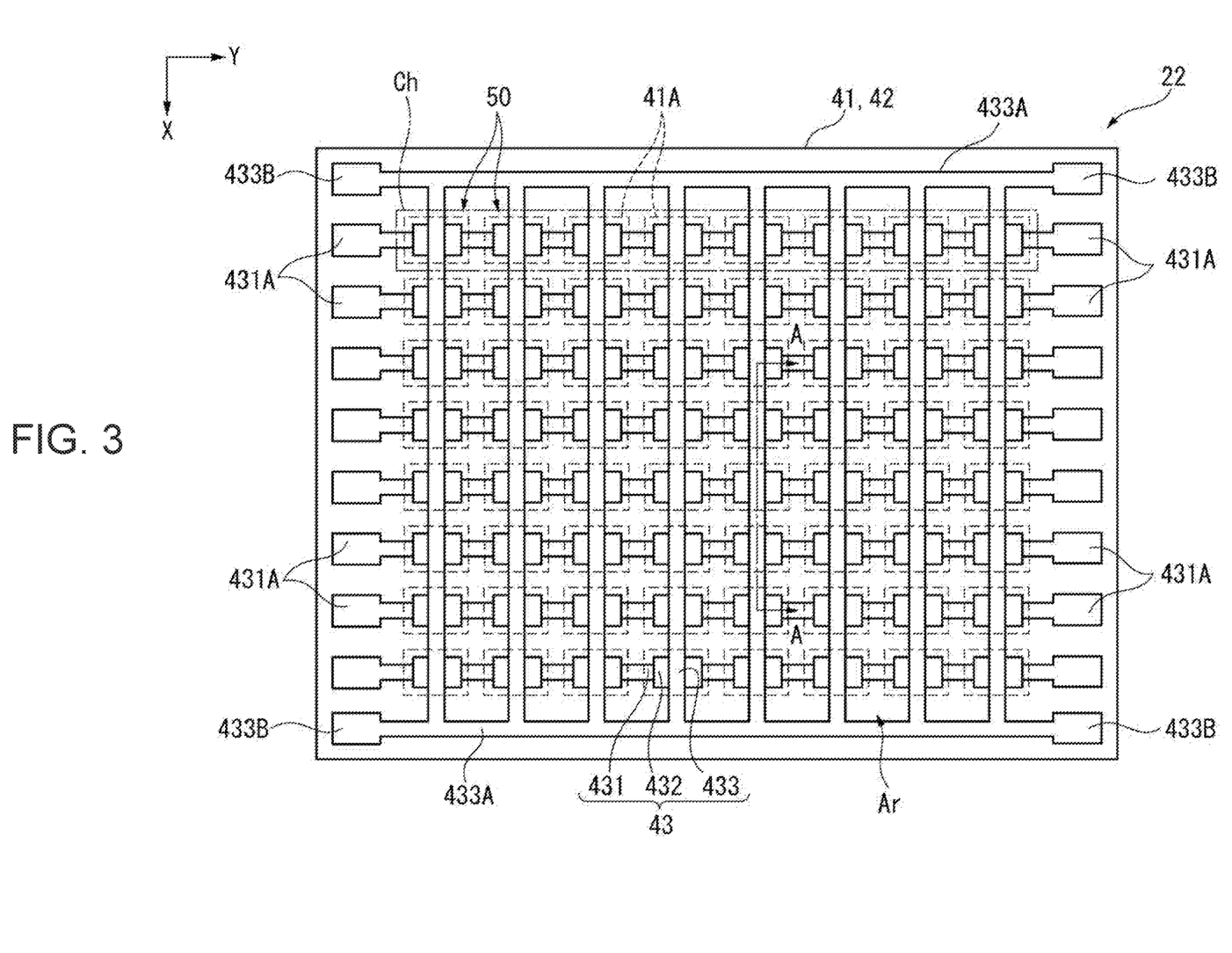
FIG. 3 is a schematic plan view of an ultrasonic device according to the first embodiment.

FIG. 3 is a plan view of the ultrasonic device 22. In FIG. 3, a sealing plate 44 (refer to FIG. 4) and an acoustic member 45 (refer to FIG. 4) are not illustrated.

As illustrated in FIG. 3, in the ultrasonic device 22, a plurality of ultrasonic transducers 50 are disposed in a two-dimensional array form along an X direction (scanning direction) and a Y direction (slice direction) intersecting (in the present embodiment, as an example, orthogonal to) each other. In the present embodiment, a transmission/reception row Ch (electrode group) of one channel (CH) is formed of a plurality of ultrasonic transducers 50 disposed in the Y direction. The transmission/reception row Ch of one CH is arranged in a plurality along the Y direction such that the ultrasonic device 22 of a one-dimensional array structure is configured. Here, a region in which the ultrasonic transducers 50 are disposed is referred to as an array region Ar.

For convenience of description, in FIG. 3, the number of disposed ultrasonic transducers 50 is reduced, but, actually, more ultrasonic transducers 50 are disposed.

Figure 4:
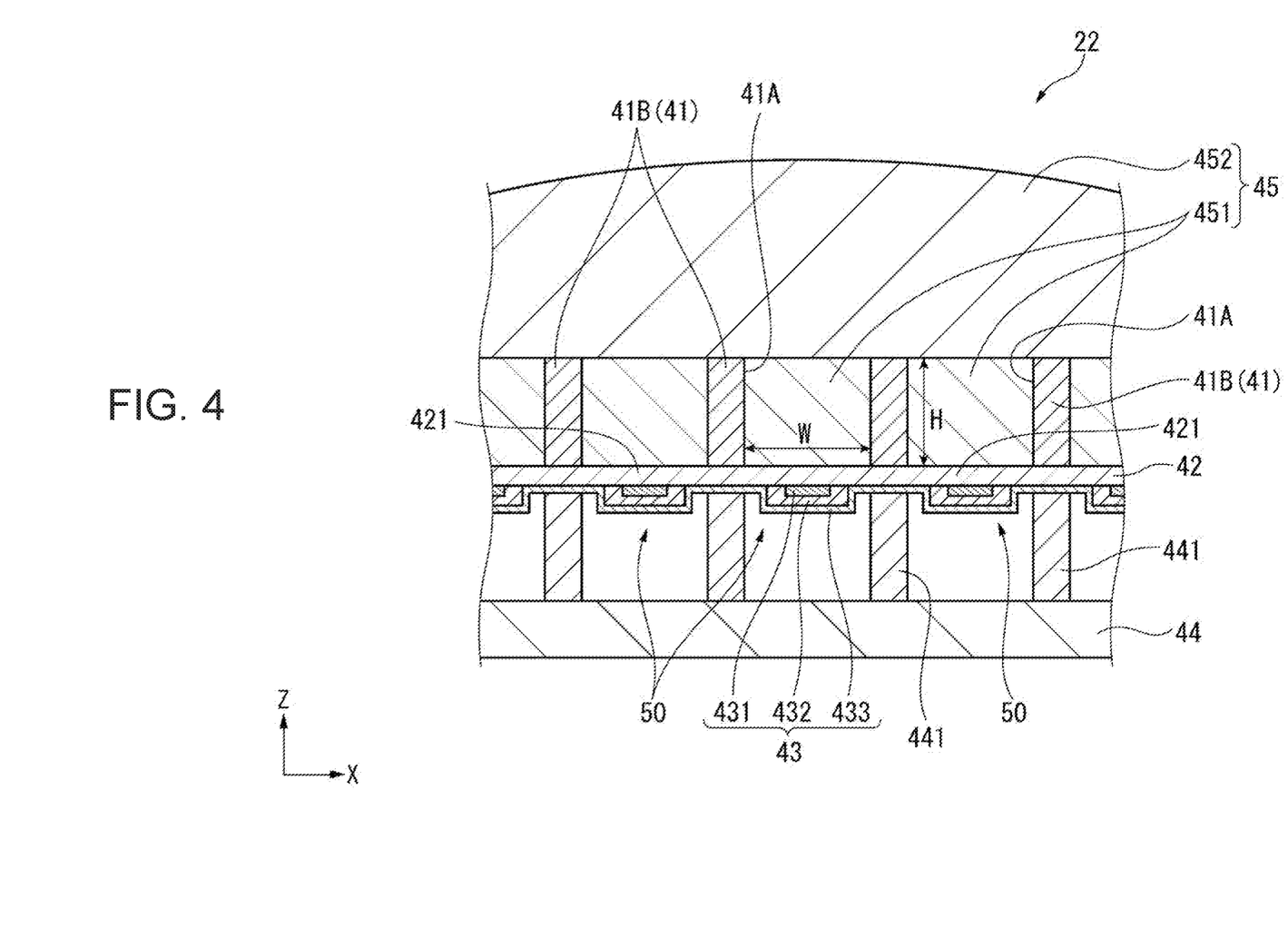
FIG. 4 is a sectional view of the ultrasonic device taken along the line A-A in FIG. 3.

FIG. 4 is a sectional view of the ultrasonic device 22 taken along the line A-A in FIG. 3.

As illustrated in FIG. 4, the ultrasonic device 22 is configured to include an element substrate 41, a support film 42, a piezoelectric element 43, a sealing plate 44, and an acoustic member 45.

Configuration of Element Substrate 41

The element substrate 41 is formed of, for example, a semiconductor substrate such as Si. The element substrate is provided with openings 41A corresponding to the respective ultrasonic transducers 50. In the present embodiment, each opening 41A is a penetration hole which penetrates through the element substrate 41 in a substrate thickness direction, and the support film 42 is provided on one end side (sealing plate 44 side) of the penetration hole. Here, a portion of the element substrate 41 joined to the support film 42 is a partition wall 41B, and the opening 41A is formed as a result of being surrounded by the partition walls 41B on four sides (±X sides and ±Y sides). In other words, the partition walls 41B located on the ±X sides of the opening 41A face each other with the opening 41A interposed therebetween, and the partition walls 41B located on the ±Y sides of the opening 41A face each other with the opening 41A interposed therebetween. Here, in the present embodiment, regarding an opening width dimension of the opening 41A, a width dimension of the opening 41A in the Y direction is larger than a width dimension thereof in the X direction, and thus the opening 41A has a rectangular shape.

Configuration of Support Film 42

The support film 42 is formed of, for example, a laminate of $SiO_2$ and $ZrO_2$, and is provided to cover the entire element substrate 41 on the sealing plate 44 side. In other words, the support film 42 is supported by the partition walls 41B forming the opening 41A, and closes the opening 41A on the sealing plate 44 side. A thickness dimension of the support film 42 is sufficiently smaller than a thickness dimension of the element substrate 41.

Here, a portion of the support film 42 closing the opening 41A forms a vibration portion 421, and a single ultrasonic transducer 50 is formed of the vibration portion 421 and the piezoelectric element 43.

The piezoelectric element 43 is provided on each vibration portion 421. The piezoelectric element 43 is formed of, for example, a laminate obtained by laminating a lower electrode 431, a piezoelectric film 432, and an upper electrode 433 from the support film 42 side.

In the ultrasonic transducer 50, a rectangular wave voltage (drive signal) having a predetermined frequency is applied between the lower electrode 431 and the upper electrode 433, so that the piezoelectric film 432 is bent, and thus the vibration portion 421 vibrates such that an ultrasonic wave is sent. If the vibration portion 421 vibrates due to an ultrasonic wave (reflected wave) reflected from a subject, a potential difference occurs between upper and lower parts of the piezoelectric film 432. Consequently, the potential difference generated between the lower electrode 431 and the upper electrode 433 is detected, and thus a received ultrasonic wave can be detected.

In the present embodiment, as illustrated in FIG. 3, the lower electrode 431 is formed linearly along the Y direction, and connects a plurality of ultrasonic transducers 50 forming the transmission/reception row Ch of one CH to each other. The drive terminals 431A are provided at both ends of the lower electrode 431. The drive terminals 431A are electrically connected to the circuit substrate.

The upper electrode 433 is formed linearly along the X direction, and connects the ultrasonic transducers 50 arranged in the X direction to each other. Ends of the upper electrode 433 on the ±Y sides are connected to common electrode lines 433A. The common electrode line 433A connects a plurality of upper electrodes 433 disposed in the X direction to each other, and is provided with the common terminals 433B electrically connected to the circuit substrate at ends thereof.

Configuration of Sealing Plate 44

A planar shape of the sealing plate 44 viewed from the thickness direction is formed to be the same as, for example, that of the element substrate 41, and is formed of a semiconductor substrate such as Si or an insulator substrate. A material or a thickness of the sealing plate 44 influences frequency characteristics of the ultrasonic transducer 50, and is thus preferably set on the basis of a center frequency of an ultrasonic wave which is transmitted and received in the ultrasonic transducer 50.

The sealing plate 44 is joined to, for example, a portion of the support film 42 supported at the partition wall 41B via a beam portion 441 made of a resin member such as a resist. Consequently, a gap having a predetermined dimension is provided between the sealing plate 44 and the vibration portion 421 in a region facing the vibration portion 421, and thus vibration of the vibration portion 421 is not hindered. Since the beam portion 441 is provided in the region of the support film 42 supported at the partition wall 41B, it is possible to prevent the occurrence of a problem (crosstalk) that a back wave from each ultrasonic transducer 50 is incident to another ultrasonic transducer 50 adjacent thereto.

The sealing plate 44 is provided with a connection portion which connects the drive terminals 431A and the common terminals 433B to the circuit substrate 23 at positions facing the respective terminals (the drive terminals 431A and the common terminals 433B) of the element substrate 41. The connection portion may have an exemplary configuration including, for example, openings provided in the sealing plate 44, and a wiring member (a flexible printed circuits (FPC), cables, or wires) connecting the respective terminals (the drive terminals 431A and the common terminals 433B) to the circuit substrate 23 via the openings.

Configuration of Acoustic Member 45

The acoustic member 45 is provided on the +Z side of the element substrate 41, and is configured to include an acoustic layer 451 and an acoustic lens 452.

The acoustic member 45 is preferably made of, for example, a viscoelastic material or elastomer, and is more preferably made of silicon rubber or butadiene rubber. Acoustic impedance of the acoustic member 45 is preferably acoustic impedance (for example, 1.5 MRayls in a case where a subject is a human body) close to acoustic impedance of a subject. Consequently, the acoustic member 45 causes an ultrasonic wave transmitted from the ultrasonic transducer 50 to propagate toward a subject with high efficiency, and causes an ultrasonic wave reflected inside the subject to propagate toward the ultrasonic transducer 50 with high efficiency.

The acoustic layer 451 fills each opening 41A on the +Z side of the element substrate 41. In other words, since the acoustic layer 451 fills the opening 41A, generation of an air bubble or the like is suppressed between the element substrate 41 and the acoustic layer 451.

As illustrated in FIG. 1, the acoustic lens 452 is exposed to the outside from a sensor window 21B of a casing 21. In ultrasonic measurement using the ultrasonic probe 2, the acoustic lens 452 exposed from the casing 21 is brought into contact with a surface of a subject via an acoustic material such as a gel. The acoustic lens 452 has a cylindrical shape whose section in a ZX plane is a circular arc shape, and causes an ultrasonic wave transmitted from the ultrasonic device 22 to converge at a predetermined depth position.

Opening Width Dimension of Opening 41A and Height Dimension of Partition Wall 41B

Next, a description will be made of a relationship between an opening width dimension of the opening 41A and a height dimension (a thickness dimension of the element substrate 41) of the partition wall 41B in the element substrate 41.

Figure 5:
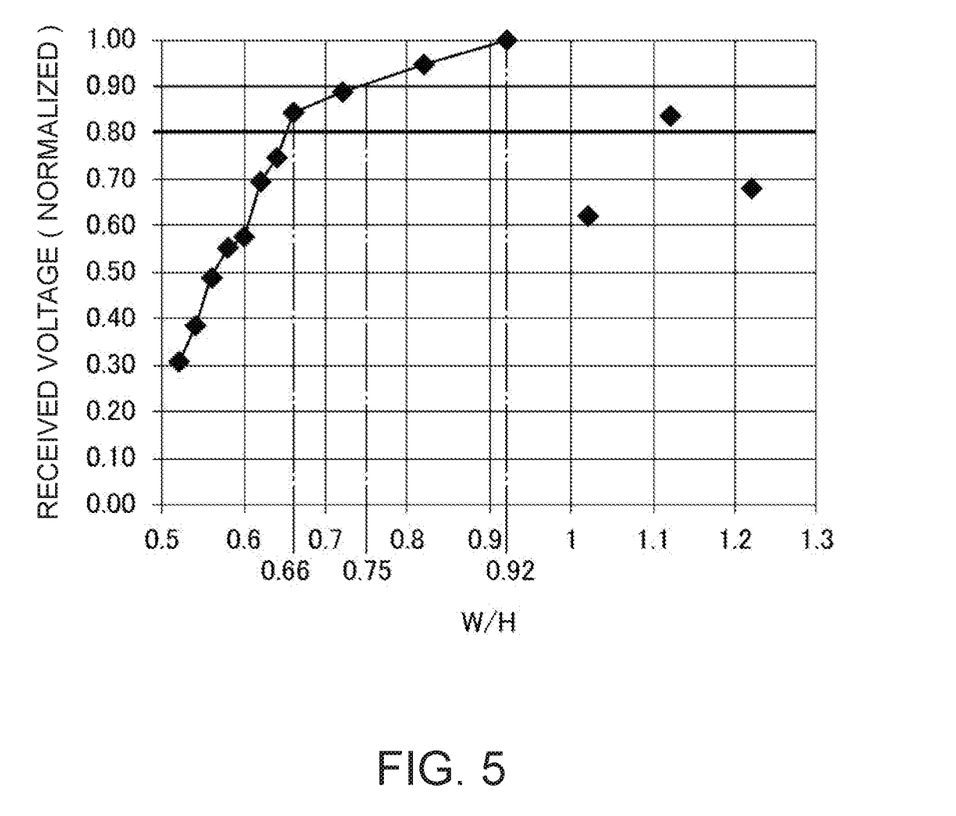
FIG. 5 is a diagram illustrating a received voltage which is output when an ultrasonic wave is received by an ultrasonic transducer at a ratio between an opening width dimension of an opening and a height dimension of a partition wall in the first embodiment.

FIG. 5 is a diagram illustrating a received voltage which is output when an ultrasonic wave is received by the ultrasonic transducer 50 at a ratio (W/H) between an opening width dimension W of the opening 41A and a height dimension (a thickness dimension of the element substrate 41) H of the partition wall 41B. In FIG. 5, a received voltage on a longitudinal axis is obtained by normalizing a value thereof with a case where the received voltage takes the maximum value as 1.

FIG. 5 illustrates received voltages of when an ultrasonic wave is transmitted from the ultrasonic transducer 50, and a reflected wave of the ultrasonic wave reflected from a subject is received. Therefore, characteristics illustrated in FIG. 5 indicate characteristics of both of the transmission sensitivity during transmission of an ultrasonic wave and reception sensitivity during reception of a reflected wave, that is, transmission/reception sensitivity of the ultrasonic transducer 50 instead of indicating the magnitude of a received voltage in a case where an ultrasonic wave with constant sound pressure is received.

An opening width dimension of the opening 41A is an important parameter for determining frequencies of ultrasonic waves transmitted and received in the ultrasonic transducer 50 or the transmission/reception sensitivity, and the width dimension W of the opening 41A in a minor axis direction has the great influence on a frequency in the ultrasonic transducer. In other words, in the present embodiment, the width dimension (a dimension of the gap between the partition walls 41B disposed on the ±X sides of the opening 41A) W of the opening 41A in the X direction which is the minor axis direction has the influence on frequencies of ultrasonic waves transmitted and received in the ultrasonic transducer 50 and the transmission/reception sensitivity.

In ultrasonic measurement using the ultrasonic probe 2, an ultrasonic wave is transmitted from each ultrasonic transducer 50, and then a reflected wave from a subject is received. The reflected wave from the subject attenuates in the subject. Here, in a case where a normalized received voltage is equal to or less than 0.8, sufficient reception sensitivity cannot be obtained, and measurement accuracy in the ultrasonic measurement is reduced.

In the present embodiment, the ratio (W/H) between the opening width dimension W of the opening 41A and the thickness dimension H of the element substrate 41 is 0.66 to 0.92.

Here, in a case where the ratio (W/H) is less than 0.66, a received voltage (normalized) of when a reflected wave is received is less 0.8, and thus the transmission/reception sensitivity in the ultrasonic transducer 50 is reduced. On the other hand, in a case where the ratio (W/H) exceeds 0.92, as illustrated in FIG. 5, a value of a received voltage (normalized) rapidly changes. Thus, it is difficult to maintain stable transmission/reception sensitivity.

In contrast, as described above, in a case where the ratio (W/H) is 0.66 to 0.92, a value of a received voltage (normalized) is 0.8 to 1.0, so that the transmission/reception sensitivity can be increased, there is no rapid change in a voltage, and stable transmission/reception sensitivity can be maintained.

More preferably, the ratio (W/H) between the opening width dimension W of the opening 41A and the thickness dimension H of the partition wall 41B is 0.75 to 0.90.

Even in a case where the ratio (W/H) exceeds 0.90, high transmission/reception sensitivity can be realized up to 0.92, but, for example, there is a case where the ratio (W/H) exceeds 0.92 due to a manufacturing error or the like. In this case, as illustrated in FIG. 5, a received voltage rapidly changes, and, thus, there is concern that a received voltage is less than 0.8 depending on cases.

In contrast, in a case where the ratio (W/H) is 0.75 to 0.90, a normalized received voltage can be stably maintained to be 0.9 or more, and thus high transmission/reception sensitivity and reliability of the apparatus can be maintained.

Therefore, in the present embodiment, in a case where the element substrate 41 of the ultrasonic device 22 is manufactured, first, the type of subject or a frequency of an ultrasonic wave corresponding to a measurement depth for the subject is set. Next, the opening width dimension W of the opening 41A corresponding to the set frequency is set.

Thereafter, a thickness dimension of the element substrate 41 is set such that the ratio (W/H) between the opening width dimension W and the thickness dimension H of the element substrate 41 is 0.66 to 0.92 (preferably, 0.75 to 0.90). In this case, a thickness dimension of the element substrate 41 is preferably set such that the ratio (W/H) is 0.90. Here, in a case where it is hard to set the ratio (W/H) to 0.90 due to, for example, an arrangement space of the ultrasonic device 22 in the ultrasonic probe 2, or an arrangement relationship with other constituent components, a thickness dimension of the element substrate 41 is set such that the ratio (W/H) is within the range from 0.75 to 0.90. In a case where it is hard to set the ratio (W/H) to the range, a thickness dimension of the element substrate 41 is set such that the ratio (W/H) is within the range from 0.66 to 0.92. Consequently, it is possible to manufacture the ultrasonic device 22 in which the transmission/reception sensitivity of an ultrasonic wave is highest so as to cope with a target measurement depth or a size or the like of the ultrasonic device 22.

Advantageous Effects of Present Embodiment

The ultrasonic measurement apparatus 1 of the present embodiment includes the ultrasonic probe 2 and the control device 10, and the ultrasonic probe 2 includes the casing 21, and the ultrasonic device 22 stored in the casing 21.

The ultrasonic device 22 includes the element substrate 41 provided with the opening 41A and the partition wall 41B, the support film 42 closing one end side of the opening 41A, the piezoelectric element 43 provided on the vibration portion 421 of the support film 42. The ratio (W/H) between the opening width dimension W of the opening 41A in the minor axis direction and the thickness dimension H of the element substrate 41 is 0.66 to 0.92.

In this configuration, as illustrated in FIG. 5, a received voltage (normalized) of when a reflected wave is received in the ultrasonic transducer 50 is stabilized and is equal to or more than 0.8. Thus, it is possible to maintain the transmission/reception sensitivity in the ultrasonic transducer to be high.

Thus, also in ultrasonic measurement on a living body using the ultrasonic probe 2, it is possible to appropriately perform transmission and reception processes of ultrasonic waves with respect to the living body and thus to realize highly accurate ultrasonic measurement.

Since highly accurate ultrasonic measurement can be performed by using the ultrasonic device 22, various processes in the control device 10 can also be performed with high accuracy. For example, an internal tomographic image of a living body can be formed with high accuracy or a blood flow or blood pressure can be measured with high accuracy on the basis of a result of ultrasonic measurement.

Second Embodiment

Next, a second embodiment will be described.

In the first embodiment, a description has been made of an example in which a single ultrasonic transducer 50 is formed of a single vibration portion 421 closing a single opening 41A, and the piezoelectric element 43 provided on the vibration portion 421. In contrast, the second embodiment is different from the first embodiment in that a plurality of vibration portions are provided in a single opening, and a piezoelectric element is disposed at each vibration portion.

In the following description, the constituent elements described above are given the same reference numerals, and description thereof will be omitted or made briefly.

Figure 6:
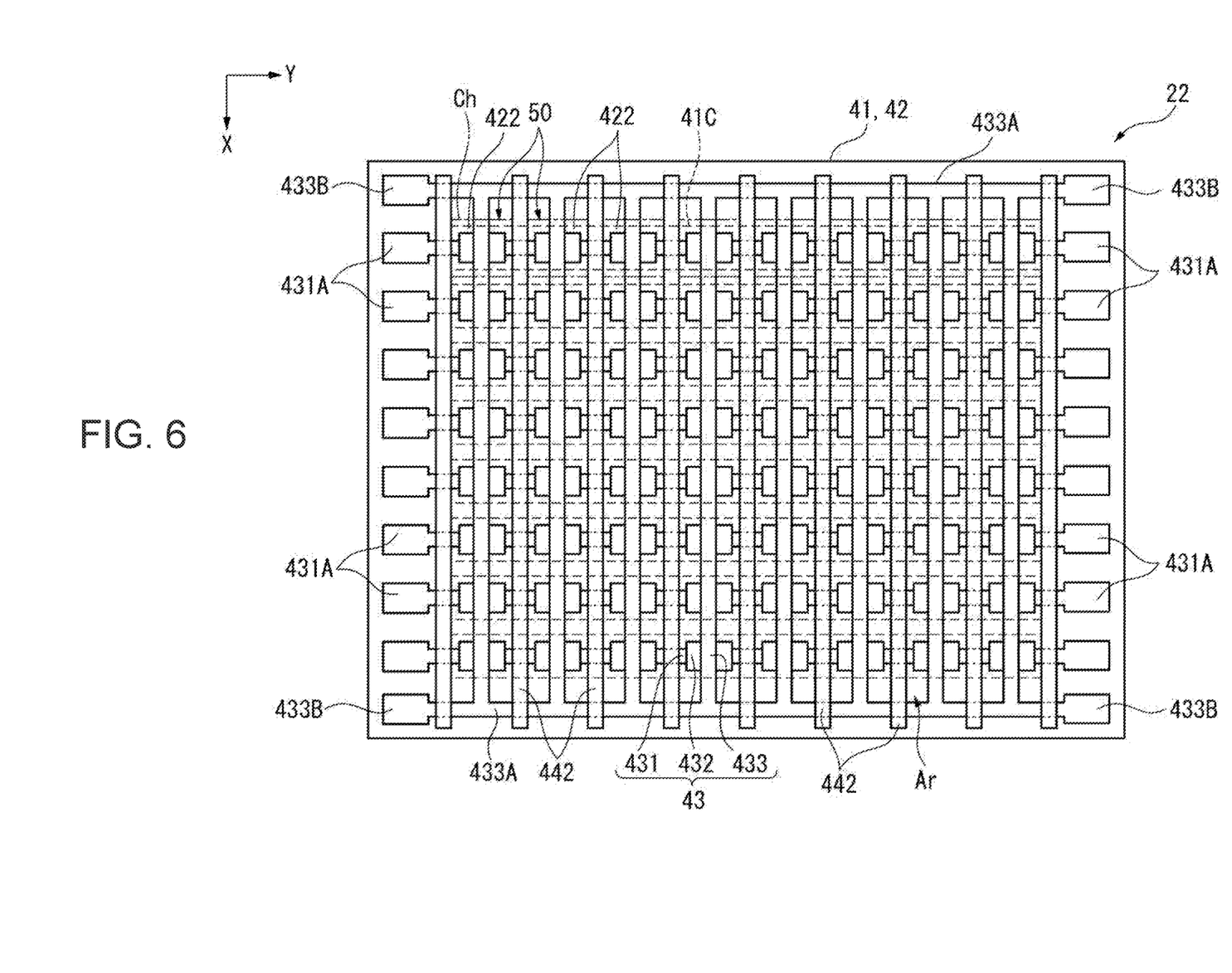
FIG. 6 is a schematic plan view of an ultrasonic device according to a second embodiment.

FIG. 6 is a plan view of the ultrasonic device 22 of the second embodiment.

Figure 7:
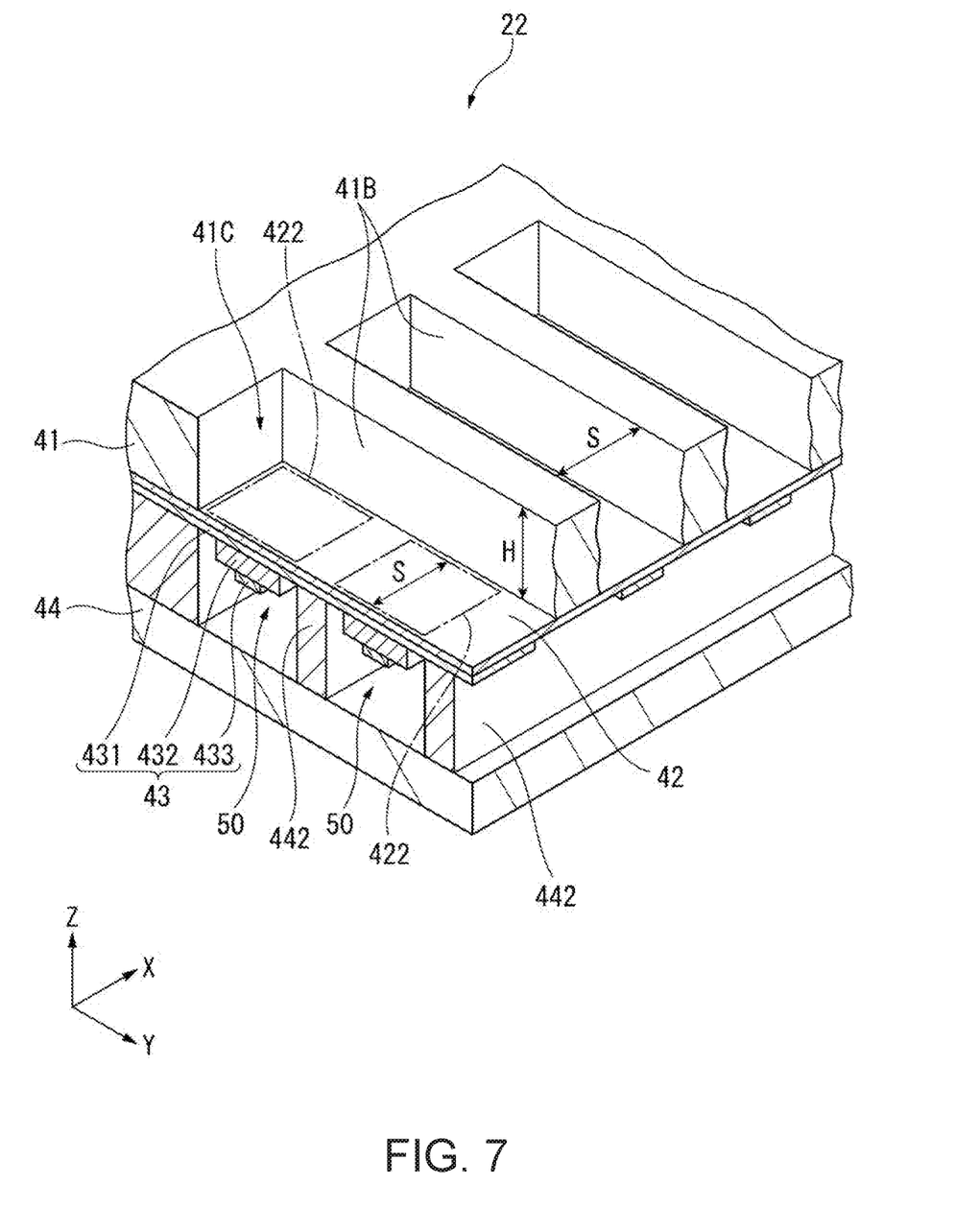
FIG. 7 is a sectional perspective view illustrating a schematic configuration of the ultrasonic device according to the second embodiment.

FIG. 7 is a sectional perspective view illustrating a schematic configuration of the ultrasonic device 22 of the second embodiment.

As illustrated in FIGS. 6 and 7, in the present embodiment, a plurality of openings 41C each of which is long in the Y direction are provided in the X direction on the element substrate 41.

Each opening 41C is a penetration hole which penetrates through the element substrate 41 in a substrate thickness direction, the support film 42 is provided on one end side (sealing plate 44 side) of the penetration hole, and the support film 42 closes one end side of the opening 41C. In the same manner as in the first embodiment, the opening 41C is formed as a result of being surrounded by the partition walls 41B on four sides such as ±X sides and ±Y sides. Therefore, the partition walls 41B located on the ±X sides face each other in the X direction, and the partition walls 41B located on the ±Y sides face each other in the Y direction.

In the same manner as in the first embodiment, the element substrate 41 is reinforced by the sealing plate 44. The sealing plate 44 is long in the X direction in at least the array region Ar, and is joined to the support film 42 via a plurality of beam portions 442 disposed at equal intervals in the Y direction.

In other words, a first surface of the support film 42 which is a surface on the element substrate 41 side is joined to the partition wall 41B, and a second surface (a rear surface of the first surface) on the sealing plate 44 side is joined to the beam portions 442.

In this configuration, the support film 42 closing the openings 41C of the element substrate 41 is divided into a plurality of regions (vibration portions 422) by edges of the partition walls 41B forming the openings 41C and edges of the beam portions 442 as illustrated in FIGS. 6 and 7.

Specifically, the vibration portion 422 is formed as a region surrounded by an edge of the partition wall 41B extending in the X direction, two edges of a pair of partition walls 41B extending in the Y direction and facing each other, and an edge of a single beam portion 442 extending in the X direction, in the support film 42 at ends of the opening 41C on the ±Y sides. In locations other than the ends of the opening 41C, the vibration portion 422 is formed as a region surrounded by two edges of a pair of partition walls 41B extending in the Y direction and facing each other, and two edges of a pair of beam portions 442 extending in the X direction and facing each other in the support film 42.

In the present embodiment, the piezoelectric element 43 is provided in each vibration portion 422. In other words, in the present embodiment, the ultrasonic transducer 50 is formed of each vibration portion 422 and the piezoelectric element 43.

Figure 8:
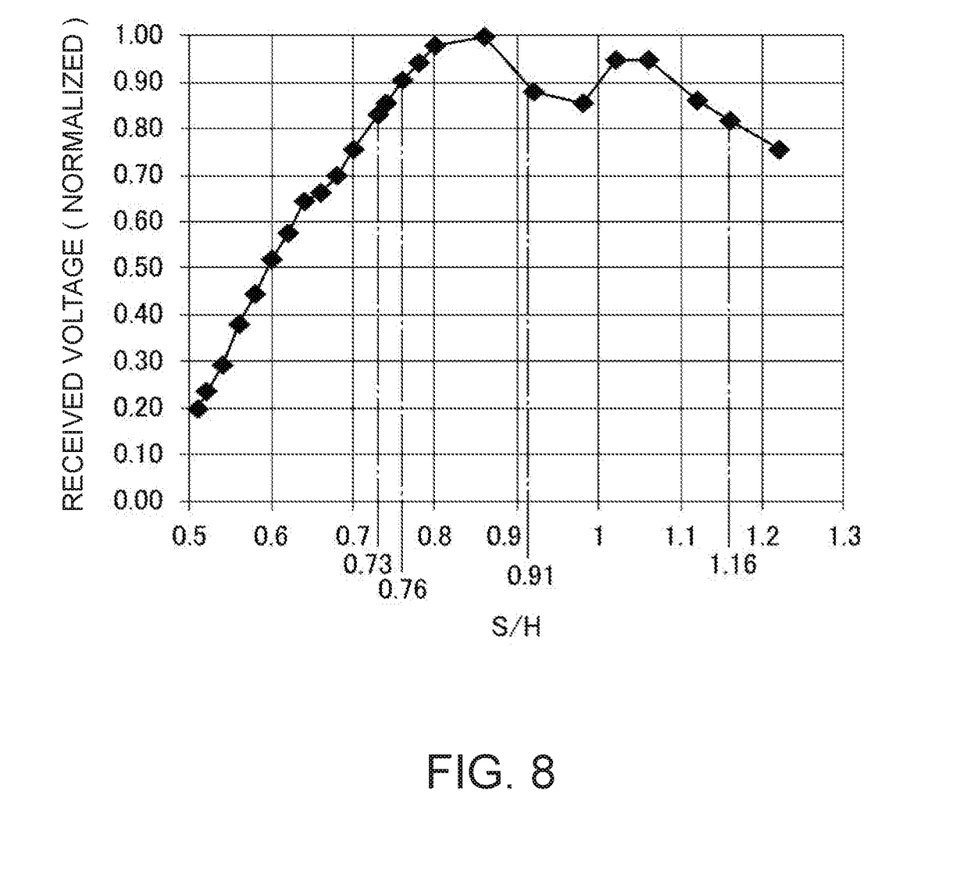
FIG. 8 is a diagram illustrating a received voltage which is output when an ultrasonic wave is received by an ultrasonic transducer at a ratio between a width dimension and a height dimension of a partition wall of a vibration portion of the second embodiment.

FIG. 8 is a diagram illustrating a received voltage which is output when an ultrasonic wave is received in the ultrasonic transducer 50 at a ratio (S/H) between a width dimension S of the vibration portion 422 of the present embodiment and a thickness dimension H of the element substrate 41. In FIG. 8, in the same manner as in FIG. 5, a received voltage on a longitudinal axis is obtained by normalizing a value thereof with a case where the received voltage takes the maximum value as 1. FIG. 8 illustrates received voltages of when an ultrasonic wave is transmitted from the ultrasonic transducer 50, and a reflected wave of the ultrasonic wave reflected from a subject is received.

Here, the width dimension S of the vibration portion 422 of the present embodiment is a dimension of a smaller distance of a distance between the partition walls 41B adjacent to each other and a distance between the beam portions 442 adjacent to each other. In the present embodiment, a distance between the partition walls 41B adjacent to each other is smaller than a distance between the beam portions 442 adjacent to each other. Therefore, the width dimension S of the vibration portion 422 is a distance between the partition walls 41B adjacent to each other.

In the same manner as in the first embodiment, also in the present embodiment, the width dimension S of the vibration portion 422 and a thickness dimension (a height dimension of the partition wall 41B) H of the element substrate 41 are set such that a received voltage (normalized) exceeds 0.8 in ultrasonic measurement using the ultrasonic probe 2.

In other words, the ratio (S/H) between the width dimension S (a distance between the partition walls 41B adjacent to each other in the present embodiment) of the vibration portion 422 and the thickness dimension H of the element substrate 41 is 0.73 to 1.16.

Here, in cases where the ratio (S/H) is less than 0.73, and exceeds 1.16, a received voltage (normalized) of when a reflected wave is received is less than 0.8, and thus the transmission/reception sensitivity in the ultrasonic transducer 50 is reduced.

In contrast, as described above, in a case where the ratio (S/H) is 0.73 to 1.16, a value of a normalized received voltage is 0.8 to 1.0, so that the transmission/reception sensitivity can be increased, and stable transmission/reception sensitivity can be realized.

The ratio (S/H) between the width dimension S of the vibration portion 422 and the thickness dimension H of the element substrate 41 is more preferably within the range from 0.76 to 0.90.

In a case of the above-described ratio (S/H), a received voltage (normalized) can be stably maintained to be 0.9 or more, and thus high transmission/reception sensitivity can be maintained. In a case where the ratio (S/H) is 1.00 to 1.10, a received voltage (normalized) can be maintained to be 0.9 or more, but there is a case where a received voltage is reduced to below 0.9 due to a manufacturing error or the like.

Therefore, in the present embodiment, in a case where the element substrate 41 of the ultrasonic device 22 is manufactured, first, the type of subject or a frequency of an ultrasonic wave corresponding to a measurement depth for the subject is set. Next, the opening width dimension S (an interval between the partition walls 41B adjacent to each other) of the opening 41A corresponding to the frequency is set.

Thereafter, a thickness dimension of the element substrate 41 is set such that the ratio (S/H) between the opening width dimension S and the thickness dimension H of the element substrate 41 is 0.73 to 1.16 (preferably, 0.76 to 0.91 or 1.00 to 1.10). In this case, a thickness dimension of the element substrate 41 is preferably set such that the ratio (S/H) is 0.86 and thus the reception sensitivity (normalized) becomes 1. Here, in a case where it is hard to set the ratio (S/H) to 0.86 due to, for example, an arrangement space of the ultrasonic device 22 in the ultrasonic probe 2, or an arrangement relationship with other constituent components, a thickness dimension of the element substrate 41 is set such that the ratio (S/H) is within the range from 0.76 to 0.91. In a case where it is hard to set the ratio (S/H) to the range, a thickness dimension of the element substrate 41 is set such that the ratio (S/H) is within the range from 1.00 to 1.10. In a case where it is harder to set the ratio (S/H) to the range, a thickness dimension of the element substrate 41 is set such that the ratio (S/H) is within the range from 0.73 to 1.16. Consequently, it is possible to manufacture the ultrasonic device 22 in which the transmission/reception sensitivity of an ultrasonic wave is highest so as to cope with a target measurement depth or a size or the like of the ultrasonic device 22.

Advantageous Effects of Present Embodiment

The ultrasonic device 22 includes the element substrate 41 provided with the opening 41C and the partition wall 41B, and the support film 42 closing one end side of the opening 41C. The first surface of the support film 42 on the element substrate 41 side is joined to the partition wall 41B, and the surface thereof which is a rear surface of the first surface on the sealing plate 44 side is joined to the beam portion 442.

The opening 41C is long in the Y direction, and a plurality of beam portions 442 each of which is long in the X direction are provided in the Y direction at positions overlapping the openings 41C in a plan view. Consequently, in the support film 42, a plurality of vibration portions 422 surrounded by edges of the partition walls 41B and edges of the beam portions 442 are obtained, and the piezoelectric element 43 is provided on the vibration portion 422.

In the present embodiment, the ratio (S/H) between the width dimension S of the vibration portion 422 in the minor axis direction and the thickness dimension H of the element substrate 41 is 0.73 to 1.16.

In this configuration, as illustrated in FIG. 8, a received voltage (normalized) of when a reflected wave is received in the ultrasonic transducer 50 is stabilized and is equal to or more than 0.8. Thus, it is possible to maintain the transmission/reception sensitivity in the ultrasonic transducer to be high.

Modification Examples

The invention is not limited to the above-described embodiments, and includes configurations obtained through modifications and alterations within the scope in which the object of the invention can be achieved, and combinations of the respective embodiments.

For example, in the second embodiment, a description has been made of an exemplary configuration in which each opening 41C is long in the Y direction, but this is only an example. For example, the opening 41C may be formed to be long in the X direction (scanning direction). In this case, a plurality of beam portions 442 each of which is formed to be long in the Y direction are disposed in the X direction.

In the second embodiment, a description has been made of an example in which a distance between the partition walls 41B adjacent to each other is smaller than a distance between the beam portions 442 adjacent to each other, but this is only an example. For example, a distance between the beam portions 442 adjacent to each other is smaller than a distance between the partition walls 41B adjacent to each other. In this case, the width dimension S of the vibration portion 422 is a distance between the beam portions 442 adjacent to each other.

In the second embodiment, a description has been made of an exemplary configuration in which the beam portion 442 is provided over ends on the ±X sides in the array region Ar, but this is only an example.

In other words, among a plurality of openings 41C provided in the X direction, the beam portion 442 may straddle a predetermined number of openings 41C so as to be provided to be long in the X direction.

For example, the beam portion 442 may be provided from the partition wall 41B disposed on the −X side of a single opening 41C to the partition wall 41B disposed on the +X side of the opening 41C. In this case, a plurality of beam portions 442 are provided in the X direction.

In the second embodiment illustrated in FIG. 6, a description has been made of an exemplary configuration in which the beam portions 442 are provided in only the array region Ar, but this is only an example, and a joint member which joins the support film 42 to the sealing plate 44 outside the array region Ar may be provided.

The joint member may be formed of a resin member such as a resist, and may be formed in the same process as the beam portions 442. The joint member may be connected to the beam portions 442 outside the array region Ar, and may be provided separately from the beam portions 442. The joint member is preferably provided over the periphery of the array region Ar in order to improve the joint strength between the support film 42 and the sealing plate 44.

In the embodiments, as an electronic apparatus, a description has been made of an exemplary configuration in which the ultrasonic apparatus employs an organ in a subject as a measurement target, but the invention is not limited thereto.

For example, the configurations of the embodiments and each modification example are applicable to a measurement apparatus which employs various structural bodies as subjects, and detects defects of the structural bodies or examines deterioration thereof.

For example, the configurations of the embodiments and each modification example are applicable to a measurement apparatus which employs various semiconductor packages, wafers, or the like as measurement targets, and detects defects of the measurement targets.

The ultrasonic measurement apparatus performing ultrasonic measurement on a subject has been exemplified, but is not limited thereto.

For example, the configurations of the embodiments and each modification example are applicable to an ultrasonic apparatus which performs ultrasonic therapy by transmitting an ultrasonic wave to a subject.

A specific structure at the time of implementing the invention may be configured by combining the respective embodiments and modification examples with each other as appropriate within the scope of being capable of achieving the object of the invention, and may be altered to other structures as appropriate.

The entire disclosure of Japanese Patent Application No. 2017-000917 filed Jan. 6, 2017 is expressly incorporated by reference herein.

What is claimed is:

1. An ultrasonic device comprising:
a substrate having a through hole and a partition wall, the partition wall surrounding the through hole, the through hole having first and second openings opposite to each other;
a vibration plate having first and second surfaces opposite to each other, the first surface of the vibration plate closing the first opening of the through hole;
a piezoelectric element that is provided on the second surface of the vibration plate;
an acoustic layer filled into the through hole; and
an acoustic lens disposed on the substrate, the acoustic lens contacting an end of the partition wall located next to the second opening,
wherein the ultrasonic device is configured to transmit an ultrasonic wave toward a target object, and the ultrasonic device is configured to receive a reflected ultrasonic wave that is formed by reflecting the ultrasonic wave off of the target object and to output a received signal corresponding to a received voltage, and
wherein, where when an opening width dimension of the first opening is indicated by W, a thickness dimension of the substrate is indicated by H, and a ratio W/H is 0.66 to 0.92, a normalized value of the received voltage is in a range of 0.8 to 1.0.

2. An ultrasonic device comprising:
a substrate having a through hole and a partition wall, the partition wall surrounding the through hole, the through hole having first and second openings opposite to each other;
a support film having first and second surfaces opposite to each other, a vibration portion of the first surface closing the first opening of the through hole;
a beam having first and second ends, the first end being fixed to a first position of the second surface of the support film, the partition wall and the beam being overlapped each other at the first positon in a plan view;
a piezoelectric element that is provided on a second position of the second surface of the support film, the second positon of the second surface corresponding to the vibration portion of the first surface of the support film;
an acoustic layer filled into the through hole; and
an acoustic lens disposed on the substrate, the acoustic lens contacting an end of the partition wall located next to the second opening,
wherein the ultrasonic device is configured to transmit an ultrasonic wave toward a target object, and the ultrasonic device is configured to receive a reflected ultrasonic wave that is formed by reflecting the ultrasonic wave off of the target object and to output a received signal corresponding to a received voltage, and
wherein, when a width dimension of the vibration portion is indicated by S, a thickness dimension of the substrate is indicated by H, and a ratio S/H is 0.73 to 1.16, a normalized value of the received voltage is in a range of 0.8 to 1.0.

3. An ultrasonic probe comprising:
the ultrasonic device according to claim 1; and
a casing in which the ultrasonic device is stored.

4. An ultrasonic probe comprising:
the ultrasonic device according to claim 2; and
a casing in which the ultrasonic device is stored.

5. An ultrasonic apparatus comprising:
the ultrasonic device according to claim 1; and
a controller that controls the ultrasonic device.

6. An ultrasonic apparatus comprising:
the ultrasonic device according to claim 2; and
a controller that controls the ultrasonic device.

* * * * *